(12) United States Patent
Hendry et al.

(10) Patent No.: US 11,053,321 B2
(45) Date of Patent: Jul. 6, 2021

(54) ERBB2 SIGNALING AND NERVE REGENERATION

(71) Applicant: THE HOSPITAL FOR SICK CHILDREN, Toronto (CA)

(72) Inventors: James M. Hendry, Toronto (CA); Eva Placheta, Vienna (AT); Tessa Gordon, Toronto (CA); Gregory H. Borschel, Toronto (CA)

(73) Assignee: THE HOSPITAL FOR SICK CHILDREN, Toronto (CA)

( * ) Notice: Subject to any disclaimer, the term of this patent is extended or adjusted under 35 U.S.C. 154(b) by 0 days.

(21) Appl. No.: 16/431,082

(22) Filed: Jun. 4, 2019

(65) Prior Publication Data

US 2019/0352424 A1 Nov. 21, 2019

Related U.S. Application Data

(62) Division of application No. 15/308,267, filed as application No. PCT/CA2015/050500 on May 4, 2015, now abandoned.

(60) Provisional application No. 61/987,692, filed on May 2, 2014.

(51) Int. Cl.
*A61K 39/395* (2006.01)
*C07K 16/28* (2006.01)
*C07K 16/32* (2006.01)
*A61P 25/02* (2006.01)
*A61K 39/00* (2006.01)

(52) U.S. Cl.
CPC ........ *C07K 16/32* (2013.01); *A61K 39/39541* (2013.01); *A61P 25/02* (2018.01); *C07K 16/28* (2013.01); *A61K 2039/505* (2013.01); *C07K 2317/24* (2013.01); *C07K 2317/76* (2013.01)

(58) Field of Classification Search
CPC .... A61K 39/39541; A61P 25/02; C07K 16/28
See application file for complete search history.

(56) References Cited

PUBLICATIONS

Jackowski, British J. of Neuorosurgery 9 (1995): 303-317.*

* cited by examiner

*Primary Examiner* — Robert C Hayes
(74) *Attorney, Agent, or Firm* — Hill & Schumacher

(57) ABSTRACT

Use of an inhibitor of the ErbB2 receptor for treatment or repair of nerves and/or nerve tissues is provided. The inhibitor includes an antibody, in particular, a monoclonal antibody, for example, Herceptin. A medicament for treatment or repair of nerves and/or nerve tissues can be formulated which includes an inhibitor of the ErbB2 receptor. A pharmaceutical kit may include a medicament having an inhibitor of the ErbB2 receptor and dosing instructions for administrating the medicament for treatment or repair of nerves and/or nerve tissues. Also provided are uses of an inhibitor of the ErbB2 receptor for increasing axon regeneration, preventing neuron or glial cell death, and/or stimulating Schwann cell proliferation in a nerve stump.

9 Claims, 10 Drawing Sheets

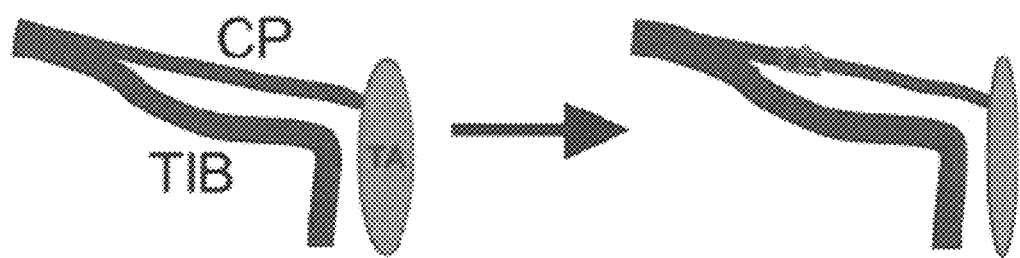
FIG. 1A
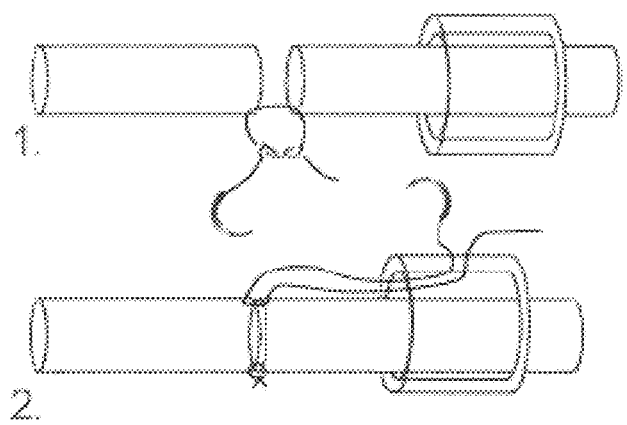
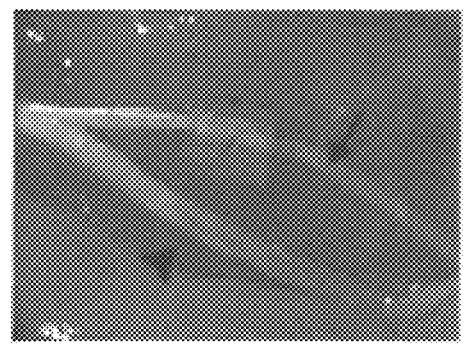
FIG. 1C
FIG. 1B

FIG. 3A
1 WEEK POST REPAIR
FIG. 3B
2 WEEKS POST REPAIR
FIG. 3C
4 WEEKS POST REPAIR
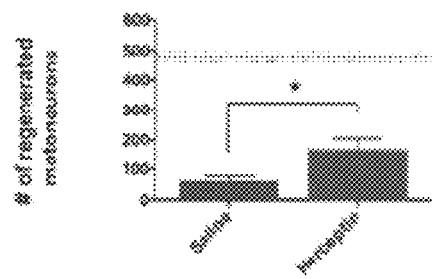
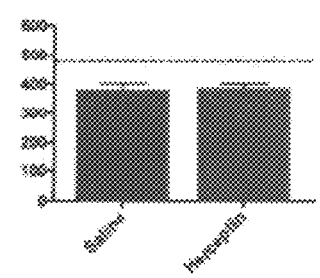
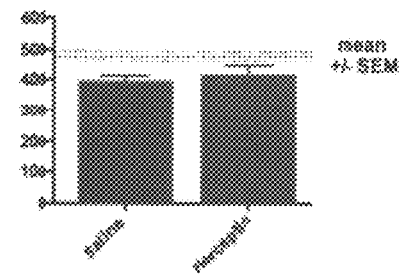
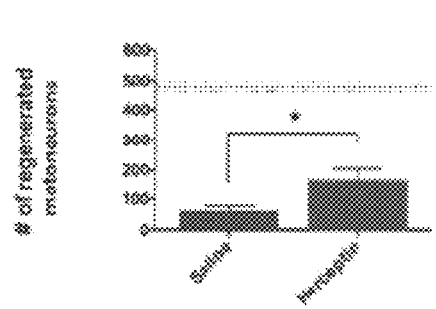
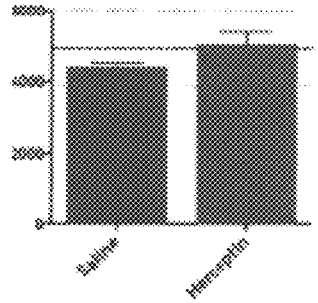
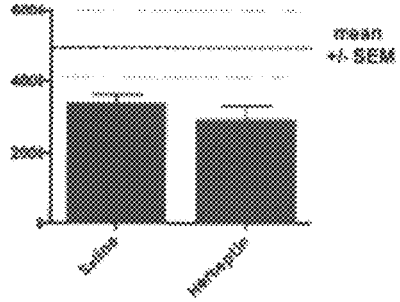
FIG. 3D
FIG. 3E
FIG. 3F FIG. 4A 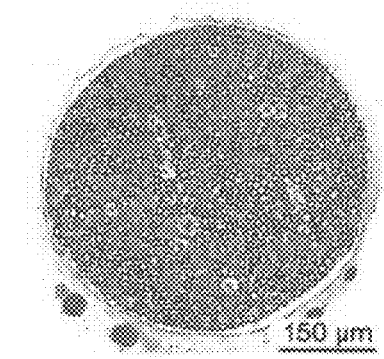 FIG. 4B 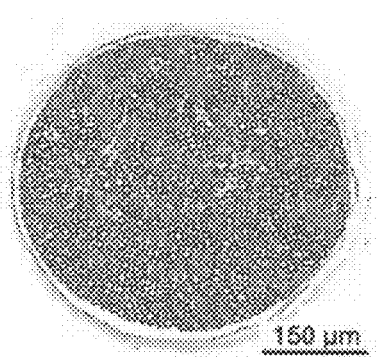
FIG. 4C 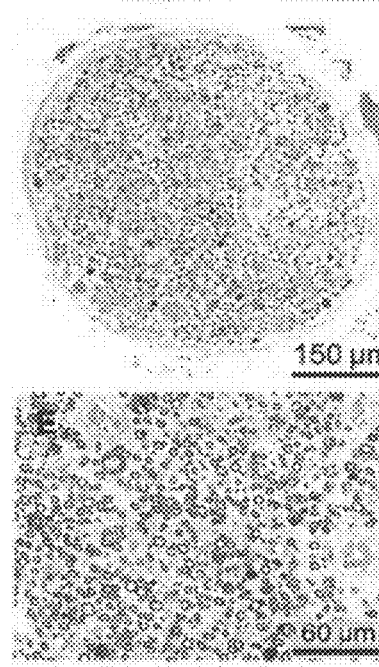 FIG. 4D 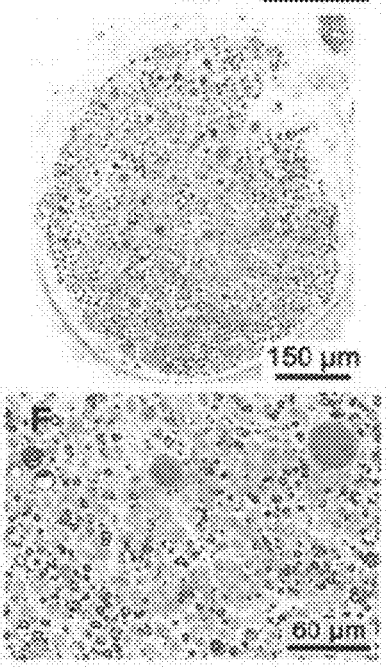
FIG. 4E FIG. 4F

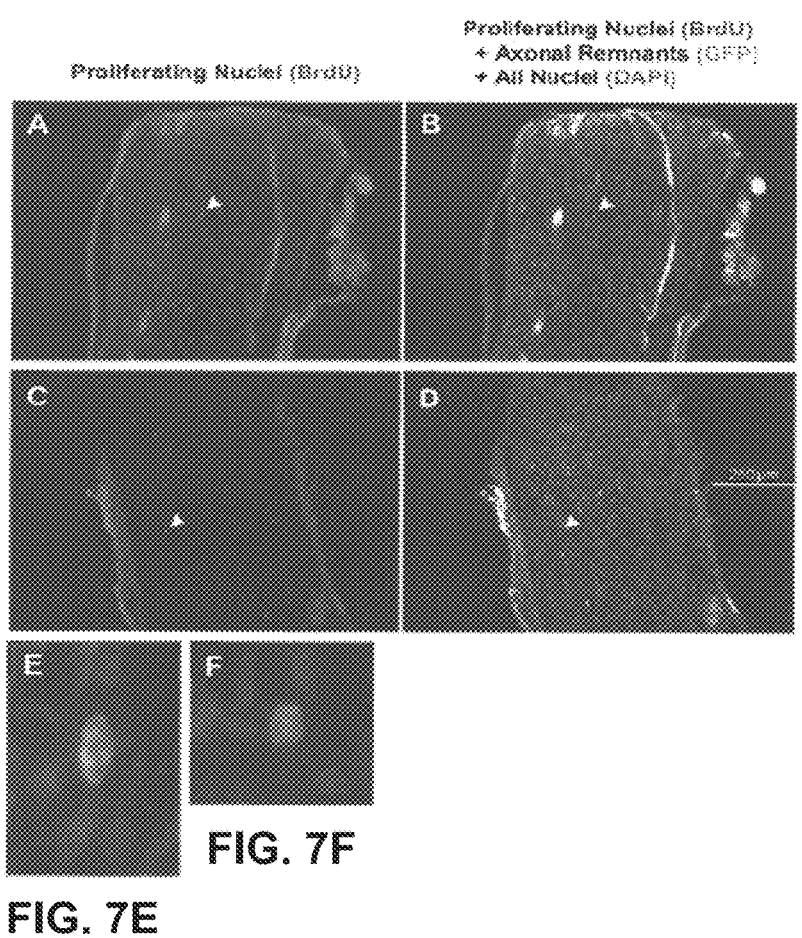

ERBB2 SIGNALING AND NERVE REGENERATION

FIELD

The present disclosure is related to methods, use and medicament for nerve regeneration, particularly peripheral nerve regeneration.

BACKGROUND

Chronic denervation is one of the harmful consequences of long regeneration times and distance that profoundly inhibits functional recovery following nerve injuries. Surgical strategies that demonstrate the ability to protect against chronic denervation may do so by supplementing the growth supportive, neurotrophic environment within the denervated nerve stump. Neuregulin, a potent Schwann cell mitogen that signals through its endogenous ErbB2 receptor is among the candidate neurotrophic factors that could mediate these effects. Neuregulin regulates several aspects of peripheral nerve regeneration, however its exact role in regulating nerve regeneration and Schwann cell proliferation is unclear.

The Schwann cell response to injury is a critical event following peripheral nerve injury because it contributes to generating an environment conducive to axonal regeneration[1-5]. This response involves de-differentiation to a non-myelinating phenotype and proliferating following loss of axonal contact after injury[5-7]. As axonal contact is reestablished with regenerating axons, Schwann cells re-differentiate back to the myelinating phenotype and produce myelin[7-9]. Importantly, the proliferation of de-differentiated Schwann cells and re-myelination of regenerated axons by re-differentiated Schwann cells is heavily reliant on the signals provided by a family of growth factors known as the 'neuregulins'[9-13].

A soluble neuregulin isoform known as glial growth factor (GGF; neuregulin type II) is upregulated within 3 days of injury and is closely associated with a characteristic surge in Schwann cell proliferation[4,8,10]. This is followed by a second wave of proliferation that occurs as the front of regenerating axons progresses distally through the nerve[8]. This second wave of proliferation is triggered by Schwann cell contact with the axon-bound neuregulin type III isoform, 'sensory and motoneuron-derived factor' (SMDF)[11]. If this second round of Schwann cell proliferation is prevented, the regenerated axons are also not myelinated. The link that this axonally-derived, membrane-bound neuregulin type III is a critical mediator of re-myelination was confirmed by conditional mutant knockout models of SMDF that demonstrated extensively hypomyelinated regenerating axons[9].

Neuregulin is a ligand for the ErbB family of receptor tyrosine kinases[13,14]. The ErbB family is a versatile group of structurally homologous membrane bound receptors that dimerize in different combinations and bind up to 11 in different ligands to transduce a diverse repertoire of signals[14-19]. Heterodimerization between two different ErbB receptors occurs through the ligand-induced extension of a 'binding loop' that forms strong intermolecular contacts with the adjacent receptor. Binding in this way facilitates trans-activation of one receptor by another through closely aligning the intracellular juxtamembrane regions that catalyze the phosphorylation of their dimer partners[20,21]. The unique phosphorylation 'signature' of tyrosine residues on the carboxy-terminal tails of the receptors is specific to each separate heterodimer combination[17,22]. Thus, different receptor combinations produce different downstream signals. These phosphorylated tyrosine residues provide docking sites for downstream signaling molecules and activation of downstream pathways[17].

ErbB2 is the preferred binding partner of ErbB3, ErbB4 and EGFR (ErbB1) and results in the strongest signaling heterodimers because it reduces ligand dissociation and provides protections against endocytic downregulation (reviewed in Citri et al., 2003). Of note, ErbB2 has no endogenous ligand of its own[18,24]. Its purpose is to act as a signal transducer for the other ligand competent ErbB family members EGFR, ErbB3 and ErbB4[14,15]. Neuregulin signals through the ErbB2-ErbB3 heterodimer combination, whereas ErbB2 is also known to strongly trans-activate EGFR[23-25]. Interestingly, EGFR has recently been implicated as a negative regulator of central nervous system axon regeneration in the presence of the inhibitory molecules myelin associated glycoprotein (MAG), chondroitin sulphate proteoglycan (CSPG) and oligodendrocyte-myelin glycoprotein (OMgp)[26,27].

Despite our current understanding of neuregulin and ErbB receptor signaling from the literature, several important questions remain. For example, Schwann cell proliferation following injury is believed to occur in response to GGF signaling. However, this model cannot explain why Schwann cell proliferation decreases after 18 days despite persistently elevated levels of GGF[10]. In addition, neuregulin signals through the trans-activation ErbB2-ErbB3 heterodimers, yet conditional knockout mutants of the ErbB2 receptor has no impact on Schwann cell proliferation at both 4 and 12 days post-injury[28]. Last, EGFR has been confirmed as an inhibitor of axon regeneration in the central nervous system, yet the factor that leads to this inhibitory trans-activation is unknown[26,27].

SUMMARY

The present disclosure aims to better characterize the role of ErbB2 in regulating nerve regeneration and to support the hypothesis that ErbB2 regulates peripheral nerve regeneration by transducing the neurotrophic signals of neuregulin. According to the present inventors, it was hypothesized that inhibition of ErbB2 with the specific monoclonal antibody Herceptin would diminish outcomes associated with peripheral nerve regeneration. This hypothesis was tested in acute and chronic injury models in the rat. The inventors show that ErbB2 inhibition with Herceptin has the paradoxical effect of accelerating early axon regeneration and stimulating Schwann cell proliferation within the denervated nerve stump. Interestingly, evidence suggests that these effects are independent of neuregulin signaling. A new, expanded role for the ErbB2 receptor in peripheral nerve regeneration is proposed that includes an inhibitory association with EGFR (ErbB1).

Disclosed herein is the use of an inhibitor of the ErbB2 receptor for treatment or repair of nerves and/or nerve tissues. The treatment or repair comprises peripheral nerve regeneration in mammals after injuries. The inhibitor may be an antibody to the ErbB2 receptor. The antibody further inhibits activation of a binding partner of the ErbB2 receptor. The binding partner is EGFR. The antibody may be a monoclonal antibody. The inhibitor may be Herceptin.

Disclosed herein is the use of an inhibitor of the ErbB2 receptor for increasing axon regeneration. The axon regeneration may be in motoneurons and/or sensory neurons.

Disclosed herein is the use of an inhibitor of the ErbB2 receptor for preventing neuron or glial cell death and/or stimulating Schwann cell proliferation in a nerve stump. The inhibitor may be Herceptin.

There is disclosed herein a medicament comprising an inhibitor of the ErbB2 receptor, wherein the medicament is for treatment or repair of nerves and/or nerve tissues. The medicament is for use in peripheral nerve regeneration after injuries. The inhibitor in the medicament is an antibody to the ErbB2 receptor. Alternatively the antibody is a monoclonal antibody. Alternatively the inhibitor is Herceptin.

Disclosed herein is a pharmaceutical kit comprising the medicament, and dosing instructions for administrating the medicament. The administration is by way of intravenous administration after injury. The administration is for one of a pre-surgical intervention, a post-surgical intervention, and a combination thereof.

There is disclosed herein a method of treating a nerve and/or nerve tissue, the method comprising administration of an inhibitor of the ErbB2 receptor. The inhibitor may be an antibody to the ErbB2 receptor, a monoclonal antibody, and the monoclonal antibody may be Herceptin. The administration of the inhibitor comprises systemically administering the inhibitor to a mammal. The damage is the result of a physical injury. Exposing the nerve to the inhibitor comprises administering the inhibitor to the mammal before or after a surgical intervention for repairing said injury. The nerve and/or nerve tissue may be damaged as a result of acquired or congenital causes.

There is disclosed a method of accelerating axon regeneration and/or preventing neuron cell death and/or schwann cell proliferation, the method comprising exposing a nerve to an inhibitor of the ErbB2 receptor.

There is disclosed a method of preventing neuron or glial cell death and/or degeneration, the method comprising exposing a nerve to an inhibitor of the ErbB2 receptor. The inhibitor may be an antibody to the ErbB2 receptor, a monoclonal antibody wherein the monoclonal antibody is Herceptin. Exposing the nerve to the inhibitor comprises systemically administering the inhibitor to a mammal.

There is provided a method of increasing Schwann cell proliferation in a nerve stump, the method comprising administering to a mammal an inhibitor of the ErbB2 receptor. The inhibitor is an antibody to the ErbB2 receptor. or the antibody is a monoclonal antibody in which the monoclonal antibody is Herceptin. The administration is systemic administration to the mammal.

A further understanding of the functional and advantageous aspects of the disclosure can be realized by reference to the following detailed description and drawings.

BRIEF DESCRIPTION OF DRAWINGS

Embodiments will now be described, by way of example only, with reference to the drawings, in which:

FIG. 1A, FIG. 1B and FIG. 1C show surgical methods for acute axotomy with immediate repair;

FIG. 3A-FIG. 3F are graphical presentations showing that administration of Herceptin enhanced motor and sensory neuron regeneration after 1, 2 and 4 week compared to controls;

FIG. 4A-FIG. 4F are representative histomorphometric cross-sections of common peroneal nerve, showing that Herceptin increased the number of axons in the distal nerve stump;

FIG. 7A-FIG. 7F show immunofluorescent staining, of longitudinal sections of common peroneal nerve 10 mm distal to the repair site, showing that Herceptin increases cellular proliferation within the distal common peroneal nerve stump 1 week following immediate repair;

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

Methods
Experimental Design

Figure 2A:
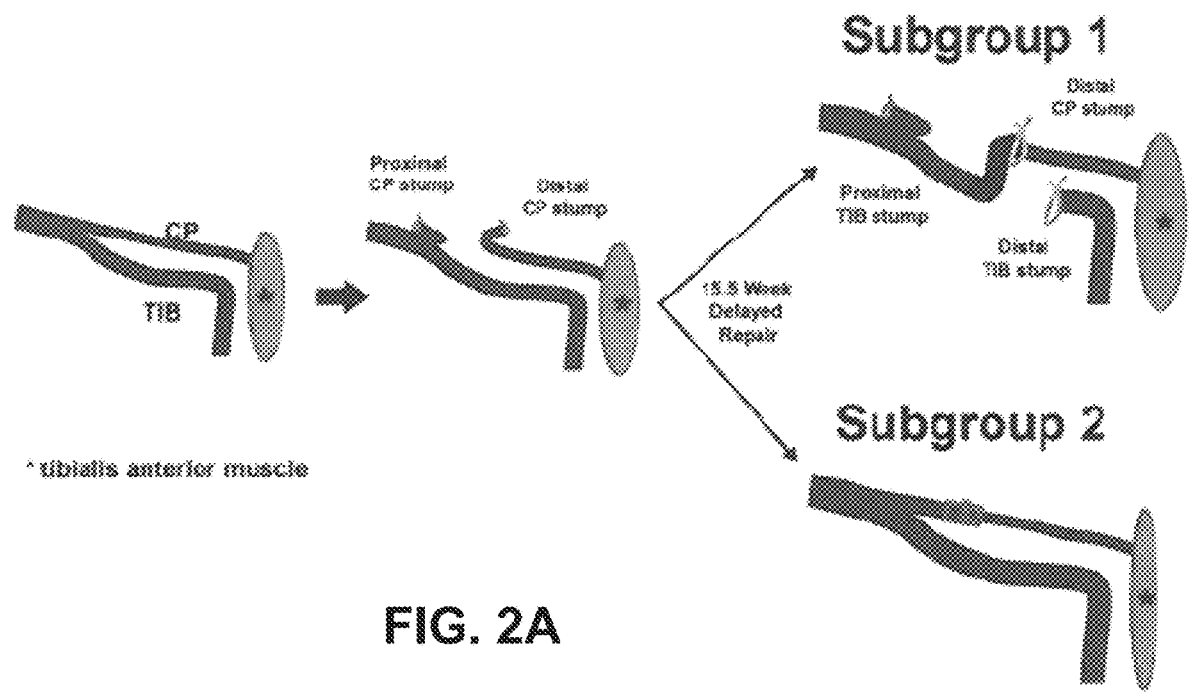
FIG. 2A and FIG. 2B show surgical methods for chronic denervation without bridge protection.
Figure 2B:
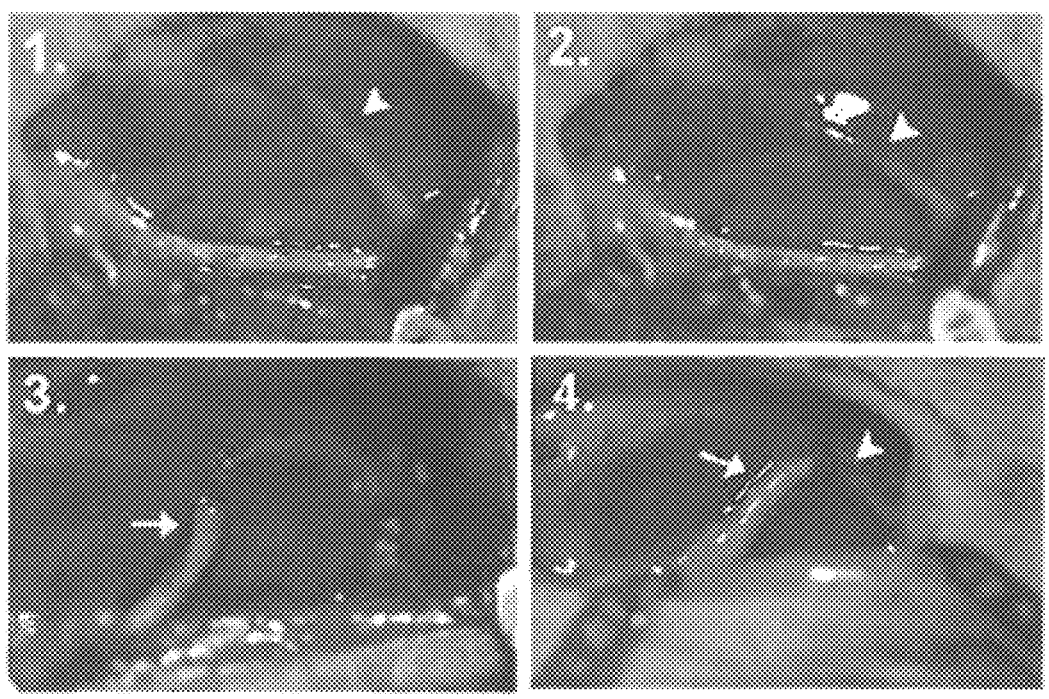

This disclosure aimed to implicate the neuregulin receptor, ErbB2, as a key regulator of axon regeneration following acute nerve transection. To this end, the common peroneal nerve of rats were transected and repaired either immediately (FIG. 1) or after a 3-month delay (FIG. 2). In the delayed repair cohort, the relative contribution of chronic denervation and chronic axotomy to regeneration in his model were isolated by repairing the denervated distal nerve stump to either an acutely or chronically axotomized proximal stump (FIG. 2A). Regeneration in all cases took place in the presence or absence of an inhibitory monoclonal antibody specific to ErbB2, Herceptin (generically known as Trastuzumab). Outcome measures in this disclosure included counting of retrogradely labeled neurons that had regenerated their axons, histomorphometry of regenerated nerves, immunohistochemistry, and Western blot analysis ErbB2 expression and activation.

Animals

Two cohorts of rats were used in this disclosure. The first cohort involved rats that underwent CP nerve transection followed by immediate repair. The second cohort involved chronically denervating the CP nerve for 3-months prior to repair. All experimental rats were in the weight range of 250-300 g. See table 1 for a summary of the experimental groups. All protocols used in this disclosure were approved by the Hospital for Sick Children's Laboratory Animal Services Committee (Toronto, Canada), and adhered strictly to the Canadian Council on Animal Care guidelines.

TABLE 1

Summary of experimental groups and used in this disclosure. Sample sizes refer to the number of nerves used in each experimental group. Bilateral surgeries were performed in all cases.
Experimental groups

| Cohort | | Group | Sample Number (n) |
|---|---|---|---|
| Immediate Repair | | 1 weeks | 8 |
| | | 2 weeks | 20 |
| | | 4 weeks | 24 |
| | | Sham | 16 |
| Delayed Repair | Acutely axotomized nerve repaired to chronically denervated stump | 2 weeks | 12 |
| | chronically axotomized nerve repaired to chronically denervated stump | 2 weeks | 10 |

Drug Administration in the Experimental Groups

Herceptin (Roche Pharmaceuticals, Hoffmann-La Roche Ltd.) is monoclonal antibodies used in human breast cancer chemotherapy that binds the 4D5 epitope on the juxtamembrane region of the ErbB2 receptor[29-31]. Rats in the experimental group received a minimum of two doses of Herceptin in the week leading up to the initial injury to ensure therapeutic serum levels existed at the time of injury. This was based on published pharmacokinetic data with a known serum half-life of 7 days in rodent[32-34]. The dosing regimen for Herceptin was intraperitoneal injections of 8 mg/kg every 3 days.

Surgical Techniques: Acute Transection with Immediate Repair

All surgical procedures were carried out under isoflurane anaesthesia and performed in an aseptic manner using standard microsurgical techniques with an operating microscope. The bilateral hind limbs of all rats were shaved and a lateral skin incision was made. The inter-muscular septum between the biceps femoris and the vastus medialis was divided and the sural, tibial (TIB), and common peroneal (CP) nerves were identified (FIG. 1).

When identified, the CP was separated from the TIB using blunt dissection as far proximally as possible without compromising the epineurium. Approximately 5 mm distal to this bifurcation, the CP nerve was transected sharply with iris scissors followed by immediate repair (FIG. 1A). The nerve was repaired with two epineurial 9-0 nylon microsutures using the technique presented in FIG. 1B and FIG. 1C. This repair technique allows two epineurial sutures to maximize epineurial alignment, but also incorporates a silicone cuff over the repair site. The incorporation of a silicone cuff over a repair site has been shown to optimize the number of regenerating axons following injury[35,36]. The wound was closed in layers. Routine post-operative monitoring and analgesia with meloxicam (~0.5 mg/kg) was provided during recovery.

In the delayed repair cohort, the surgical exposure was the same. During the denervation procedure, the proximal and distal stumps of the CP nerve were sutured in opposite directions to the innervated muscle to prevent accidently re-innervation. The repair procedure took place after a mean denervation period of 15.5 weeks. The chronically denervated distal CP nerve stump was repaired to either: 1. the acutely transected proximal stump of the adjacent TIB nerve (FIG. 2B); or 2. the chronically axotomized proximal CP nerve stump.

Retrograde Labeling:

The final surgery for each rat involved retrograde labeling using 4% (w/v) Fluorogold (Hydroxystilbamidine bis-(methanesulfonate); Sigma #39286). All the regenerated axons that were exposed to the dye transport the tracer to the cell bodies of the motoneurons in the ventral horn of the spinal cord. Bilateral surgical exposure was carried out as described above using a dissection that was carried past the knee joint for adequate exposure. The CP nerve in all cases was divided 10 mm beyond the repair site and the freshly cut nerve tip was incorporated into a Vaseline well that contained 10 µl of Fluorogold solution. Wells were created using 6×6 mm square of parafilm as the base and concentric rings of Vaseline applied with a 25 g syringe to build up the side-walls. The nerve was incubated in the retrograde dye for 1 hour. The well was then removed and the wound irrigated thoroughly. The wounds were closed in layers and the animals allowed to recover from anesthesia.

One week following the retrograde labeling procedure, animals were euthanized with an intraperitoneal injection of sodium pentobarbital. The rats underwent immediate transcardial perfusion with 240 cc of cold saline followed by 120 cc of 4% paraformaldehyde (PFA). The lumbar enlargement containing the sciatic nerve motoneurons and the L4/L5 dorsal root ganglia were harvested and fixed in a solution of 4% PFA with 30% sucrose for 5 days. All tissue was embedded in frozen OCT medium (Tissue-Tek, Andwin Scientific, CA) and the spinal cords sectioned at 50 µm onto Fisher brand Superior glass slides.

Retrogradely labeled motor and sensory neurons were counted using a fluorescent microscope. Labeled neuronal cell bodies were visualized under the correct filter depending on the dye used. Inclusion criteria for positively stained nuclei included: a well-defined cell body with clearly defined borders, uniform luminescence of the entire cell and dendrites and processes extending from the cell body.

Histomorphometry

The CP nerve was harvested 10 mm distal to the repair site, fixed in 2% glutaraldehyde, post-fixed with 1% osmium tetroxide, ethanol dehydrated, and embedded in Araldite 502 (Polyscience Inc., Warrington, Pa.). Thin (0.6 µm) sections were cut using a LKB II Ultramicrotome (LKB-Produckter A. B., Broma, Sweden) and then stained with 1% toluidine blue for examination by light microscopy. At 100× overall magnification, the entire nerve cross-section was captured using Image-Pro Analyzer version 9.0 (Media Cybernetics, Rockville, Md.) and the number, size and myelination of the axons evaluated using a custom designed program in Mat- Lab (Mathworks Inc, Natick, Mass.). The sections were evaluated for overall nerve architecture and quality of the regenerated fibers. The number of myelinated axons was counted and the nerve fiber size and myelination thickness were measured from the entire imaged nerve cross-section.

Schwann Cell Proliferation Assay:

Nerve tissue distal the repair site one week after immediate repair was assayed for cell proliferation using DNA incorporation of bromodeoxyuridine 2 hours prior to the final surgery. Rats were injected with an intraperitoneal solution of bromodeoxyuridine (Sigma) at a dose of 100 mg/kg. All active DNA replication during these two hours leading up to tissue harvest incorporate the systemically administered thymidine analogue. Tissue was fixed in 4% PFA with 30% sucrose and sectioned at 30 μm thickness. Antigen retrieval using a brief 5 minute enzymatic digestion with 0.1M proteinase K was performed. Slides were then incubated in 2M HCl for 30 minutes at room temperature to denature the double stranded DNA of all nuclei, followed by neutralization in 0.1 M Borate buffer (pH 8.3) for 5 minutes. The remainder of the immunostaining procedure followed the general immunohistochemistry protocol outlined in chapter 2. Tissue was incubated overnight with anti-BrdU antibodies (Sigma).

Separate specimens of the immediately repaired common peroneal nerve were removed from rat hindlimbs after 1 week of regeneration. The region immediately proximal and distal to the repair site were sectioned at 20 μm thickness and fixed with ice cold ethanol. These were then rinsed with 0.1% TBST buffer and incubated with blocking buffer comprised on bovine serum albumin. After rinsing the blocking agent, slides were incubated overnight with primary antibodies to anti-phospho-EGFR (Abcam). Secondary antibody stains were carried out the next day with Alexa-fluor immunofluorescent detection antibodies. These repair sites were then imaged with immunofluorescent microscopy and the fluorescent intensity of anti-phospo EGFR immunoreactivity measured with imageJ software.

Protein Quantification

Four rats underwent sciatic nerve transection and immediate surgical repair. The repaired nerve was allowed to regenerate for 7 days. Thereafter, nerve tissue distal to the repair site was harvested, snap frozen and ground into a fine powder in a mortar and pestle that was cooled with liquid nitrogen at −196° C. This powder was dissolved and incubated in a hypotonic solution (20 mM Tris (pH 7.8); 10 mM NaCl; 3 mM $MgCl_2$) that included protease inhibitor cocktail (Sigma P8340) and phosphatase inhibitors (Sigma P5726) for 15 minutes on ice. A hypotonic lysis buffer (0.5 mM EDTA, 0.6% Nonidet-p40, 0.5% Triton X100, 0.25% CHAPS, 5% sucrose, 1% deoxycholate, 10% glycerol) was added to the nerve preparation and incubated for an additional 20 minutes at 4° C. The nerve samples were then subjected to a tissue homogenizer for 60 seconds followed by sonication to further break apart and dissolve membrane bound protein. Samples were then centrifuged at 10,000 rpm for 10 minutes and the supernatant kept for analysis at 20° C.

Protein electrophoresis involved denaturing 120 μg of whole nerve lysate with ß-mercaptoethanol and loading into pre-cast 12% polyacrylamide gels (Precise Protein Gels, Pierce Thermoscience). Electrophoresis was run at 150V for 1 hour in HEPES running buffer. The transfer was run at a fixed 220 mA current for 1.5 hours. The membrane was then rinsed with Tris-buffered Saline with 0.1% Tween (TBST) and blocked with 5% BSA (w/v) in TBST for 2 hours. Anti-ErbB2 (Abcam Inc.) or anti-phospho-ErbB2 (Millipore Inc.) primary antibodies were incubated overnight at 4° C. The membrane was then washed in TBST and horseradish peroxidase (HRP) conjugated secondary antibodies were diluted (1:1000) in TBST with 5% BSA and applied for 1 hour at room temperature. ECL (Thermoscientific) was applied to activate the HRP. The membrane was imaged with a Li-COR Odyssey Chemiluminescent imager (Li-COR Biosciences, Lincoln, Nebr.).

Statistical Analysis

Normalcy of the data sets were compared using the Kolmogorov-Smirnov test (p>0.05). Comparisons of data in the experimental series #2 used a two-tailed t-test. An alpha of 0.05 was used in all cases and significance was determined if p<0.05. Means and standard error of the mean (SEM) are reported.

Results

Animal Survival:

All surgeries and intraperitoneal injections of Herceptin or saline were tolerated well with one exception. One rat in the Herceptin group died intraoperatively from anesthetic complications while undergoing retrograde labeling. The labeling could not be completed, but the CP nerve tissue distal to the surgical repair site was harvested for immunohistochemistry and histomorphometry.

Administration of Herceptin Enhances Motoneuron and Sensory Neuron Regeneration 1 Week After Immediate Repair Fifty-two common peroneal nerves from 26 rats were successfully transected and repaired immediately within a silicone tube. In many cases, excellent regeneration was observed. Bilateral retrograde labeling with Fluorogold was also successful and spinal cord sections were analyzed in a blinded fashion. There were no instances of ruptured repairs any group analyzed.

After 1 week of regeneration there was a significant increase in the number of motoneurons (FIG. 3A) that regenerated axons 10 mm beyond the repair site in rats that received Herceptin (169±37) compared to rats that received saline (62±15; p<0.05; FIG. 3A). Two weeks after repair, there was no significant difference in the number of motoneurons (FIG. 3B) that regenerated their axons between rats that were injected with Herceptin (386±15) versus saline (382±20) (FIG. 3B). Similarly, there was no difference in the number of motoneurons (FIG. 3C) regenerating axons 4 weeks following repair between Herceptin (417±28) and Saline (398±16) treated animals (FIG. 3C). Overall, the extent of regeneration among all groups was excellent and reached a mean number of regenerated neurons that was 84% that of un-injured controls.

A similar trend was noted with sensory neuron regeneration, where significantly greater numbers of sensory neurons regenerated 10 mm beyond the repair site after 1 week in the group that received Herceptin (1099±237) compared with saline controls (294±37) (FIG. 3D). There was no significant difference in the number of regenerated sensory neuron regeneration after 2 weeks (5056±340 vs saline—4453±110; FIG. 3E) or 4 weeks (2920±411 vs 3413±218; FIG. 3F) when comparing Herceptin and saline control treated animals, respectively.

Herceptin Administration Increases the Number of Myelinated Axons Regenerating into the Acutely Denervated Common Peroneal Nerve.

The CP nerve was harvested 10 mm distal to the site of transection and surgical repair for histomorphometric analysis 2 and 4 weeks after repair. The nerve samples obtained from the animals 2 weeks after repair could not be analyzed, as very few axons were myelinated at the harvest site and most of the axons had morphological evidence of Wallerian degeneration. In the 4 week group, nerve cross sections from rats treated with Herceptin demonstrate increased density of regenerated, myelinated fibers (FIG. 4C, FIG. 4E) compared with rats treated with saline (FIG. 4D, FIG. 4F). There was no visible difference between the nerves of sham-operated animals from either Herceptin (FIG. 4A) or saline (FIG. 4B) groups.

Figure 5A:
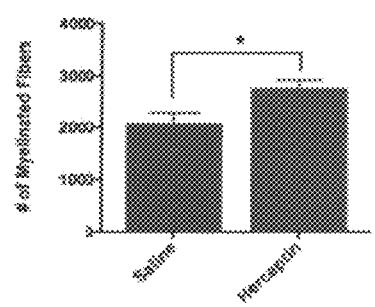
FIG. 5A-FIG. 5F are graphical representation of quantitative analysis showing that Herceptin increased the number of myelinated axons in the distal nerve stump.
Figure 5B:
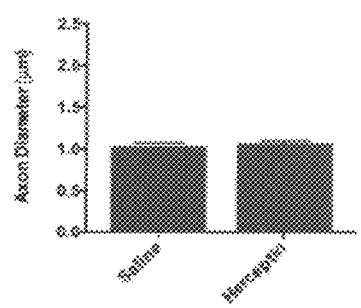
Figure 5C:
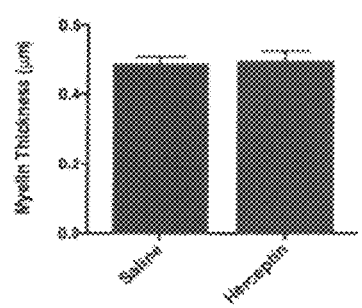
Figure 5D:
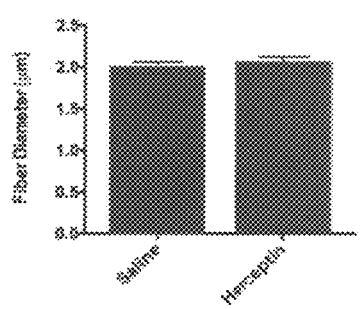
Figure 5E:
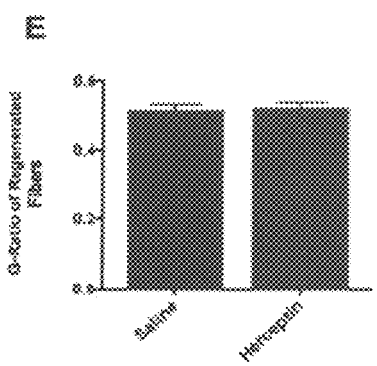
Figure 5F:
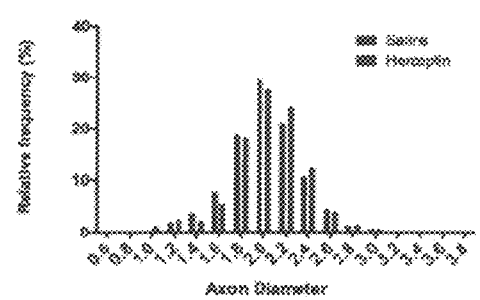

Quantitative analysis of these nerve sections revealed that there were significantly more myelinated axons in the Herceptin group (2752±180) than in the saline group (2071±220) ($p<0.05$) 4 weeks following immediate repair (FIG. 5A). There were no significant differences in the fiber and axon diameters, myelin thicknesses or the distributions of fiber diameters in the Herceptin-treated animals compared to controls at 4 weeks post-repair (FIG. 5B to FIG. 5F).

Administration of Herceptin Does Not Alter the Levels of ErbB2 Phosphorylation Distal to the Repair Site.

Figure 6A:
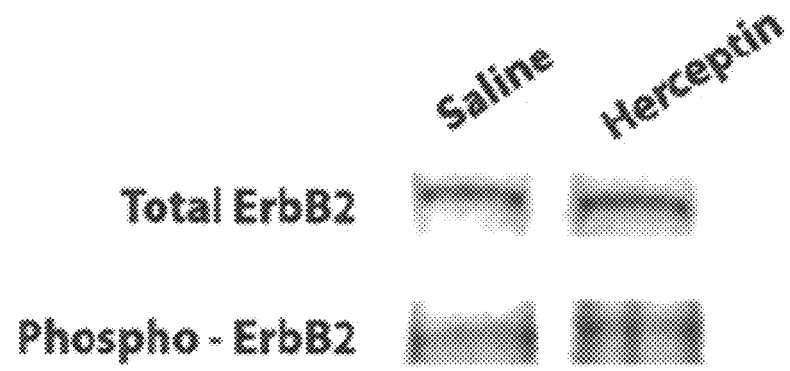
FIG. 6A and FIG. 6B show electrophoresis of whole nerve distal stump lysate, confirming that Herceptin does not downregulate activation of ErbB2, but does downregulate the second messenger Akt.
Figure 6B:
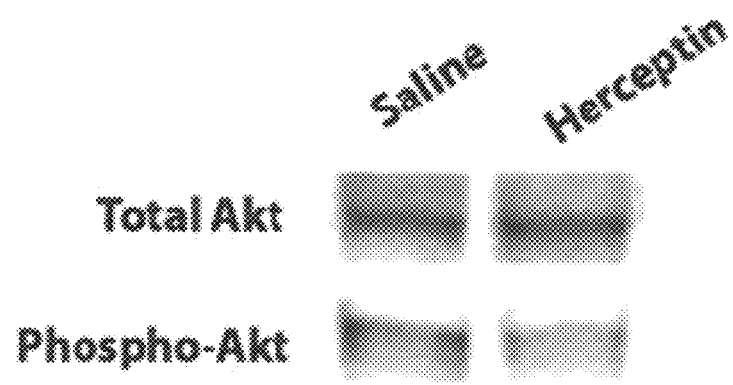

Protein electrophoresis of whole tissue lysate of nerve distal to the transection site revealed that the total amount of expressed ErbB2 in regenerating CP nerves was the same between rats that received Herceptin or saline (FIG. 6A). Interestingly, although there was no difference in the expression of activated, phosphorylated ErbB2 (FIG. 6A), Herceptin did, nonetheless, exert its anticipated biological effect by decreasing the activation of Akt, a second messenger downstream from ErbB2 (FIG. 6B).

Herceptin Administration Increases Cellular Proliferation in Nerve Tissue Distal to the Repair Site After 1 Week.

Each rat received 100 mg/kg of intraperitoneal bromodeoxyuridine (BrdU) 2 hours prior to the onset of retrograde labeling surgery at 2 and 4 weeks. Chemical injections were tolerated well by the rats and no complications were observed from administration. The segment of nerve tissue remaining after the histomorphometry specimen was harvested was fixed in 4% paraformaldehyde with 30% sucrose. After immunofluorescent staining, a greater number of cells in the nerve sections from rats received with Herceptin had incorporated the BrdU antigen compared to rats that received saline (FIG. 7A, FIG. 7C). This indicates that there were more mitotically active, proliferating cells in nerves from rats treated with Herceptin. All BrdU labeled nuclei overlapped with non-specifically stained DAPI nuclei (FIG. 7B, FIG. 7D). Also note the abundance of axonal debris present from active Wallerian degeneration 1 week after injury and repair.

Figure 8A:
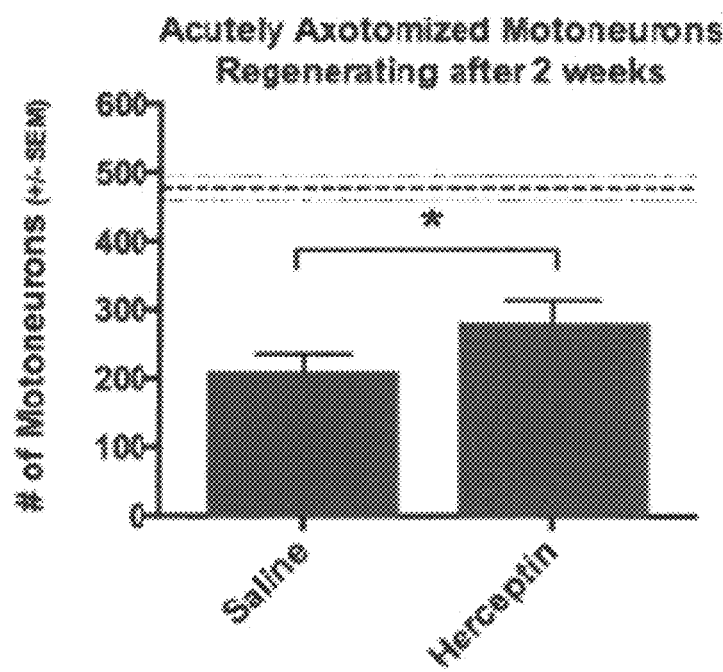
FIG. 8A and FIG. 8B are graphical representation of the effects of chronic vs. acute axotomy on regeneration, showing that Herceptin increases the number acutely axotomized motoneurons that regenerated into chronically denervated distal CP stump.
Figure 8B:
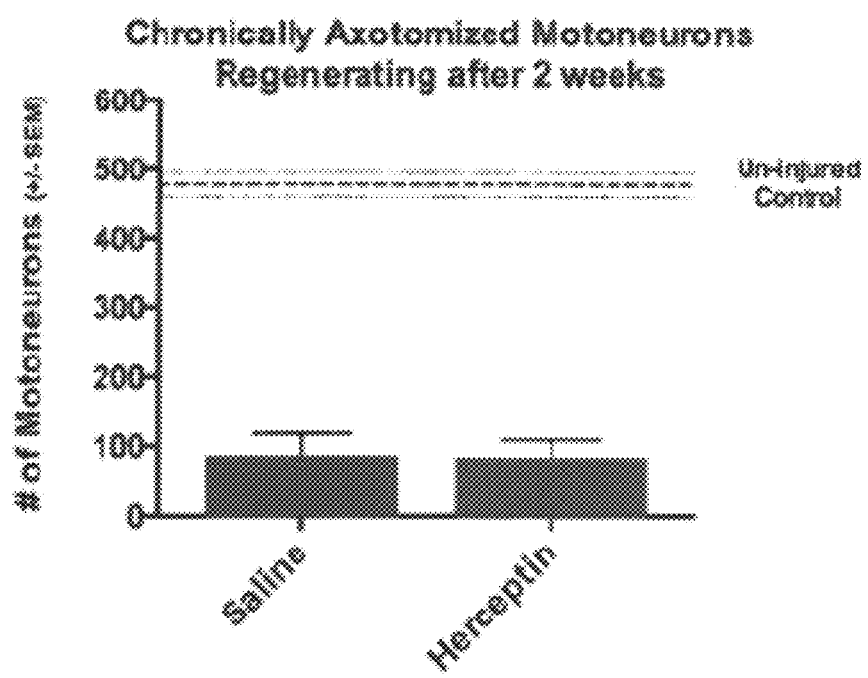

Herceptin Enhances Regeneration when Acutely, But Not Chronically Axotomized Motoneurons and Sensory Neurons Regenerate Their Axons within a Chronically Denervated Nerve Stump The effect of Herceptin's inhibition on ErbB2 was examined with the two repair strategies after 15.5 weeks of chronic denervation. Isolating the effects of chronic vs. acute axotomy on regeneration with these different repair techniques identified that Herceptin enhanced the outgrowth of axons from acutely but not chronically axotomized motoneurons when compared against saline treated animals from the same groups. After 2 weeks of regeneration, the number of freshly axotomized motoneurons that regenerated into the chronically denervated distal CP nerve stump was significantly higher in rats that received Herceptin (282±31) compared to rats that received saline (210±24) injections (FIG. 8A). When the chronically axotomized proximal CP nerve stumps were repaired to the distal denervated CP stumps there was no difference in the number of motoneurons that regenerated axons in rats injected with Herceptin (84±25) compared with those injected with saline (87±32) after 2 weeks of regeneration (FIG. 8B). This is informative considering that there was no difference in the regenerative environment within the chronically denervated distal CP nerve stumps. Therefore, action of Herceptin appears to be directed toward axons or Schwann cells in the proximal stump.

A similar trend was noted with sensory neuron regeneration, where significantly greater numbers of sensory neurons were regenerated after 2 weeks compared with saline controls. When the chronically axotomized proximal CP sensory stumps were repaired to the distal denervated CP stumps there was no difference in the number of sensory neurons that regenerated axons in rats injected with Herceptin compared with those injected with saline after 2 weeks of regeneration.

Figure 9A:
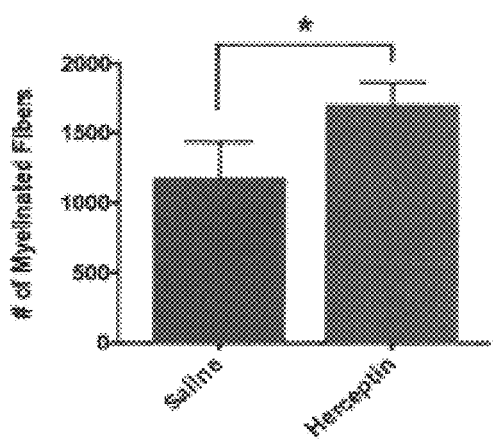
FIG. 9A-FIG. 9E are graphical representations showing that the ErbB2 inhibitor Herceptin significantly increases the number of acutely axotomized myelinated fibers regenerated into a 15.5 week chronically denervated CP nerve stump.
Figure 9B:
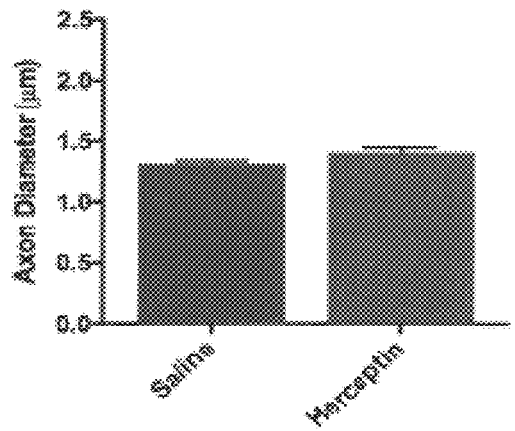
Figure 9C:
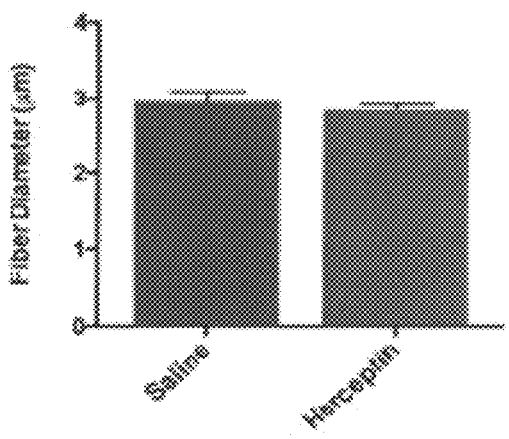
Figure 9D:
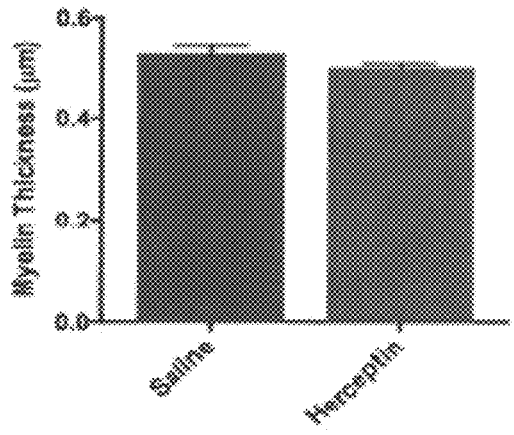
Figure 9E:
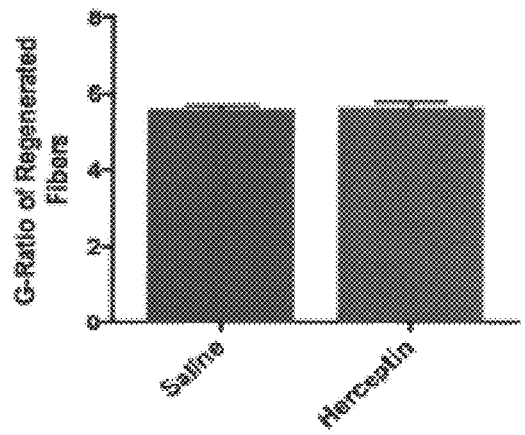

Herceptin Administration Increases Axonal Outgrowth of Acutely Axotomized Motoneurons into the Distal Denervated CP Nerve Stump Histomorphometry of nerve sections removed 10 mm distal to the repair site were analyzed. When the freshly transected TIB nerve was cross-sutured to the chronically denervated distal CP stump, it was found that there was a significant increase in the total number of myelinated fibers in rats treated with Herceptin (1714±156) compared to rats that received saline (1178±262) (FIG. 9A). There was no other differences between nerve sections from rats treated with Herceptin or saline when comparing axon diameter, myelin thickness, total fiber diameter or g-ratio (FIG. 9B-FIG. 9E)

Herceptin Administration Decreases EGFR Phosphorylation in the Regenerating Common Peroneal Nerve.

Figure 10A:
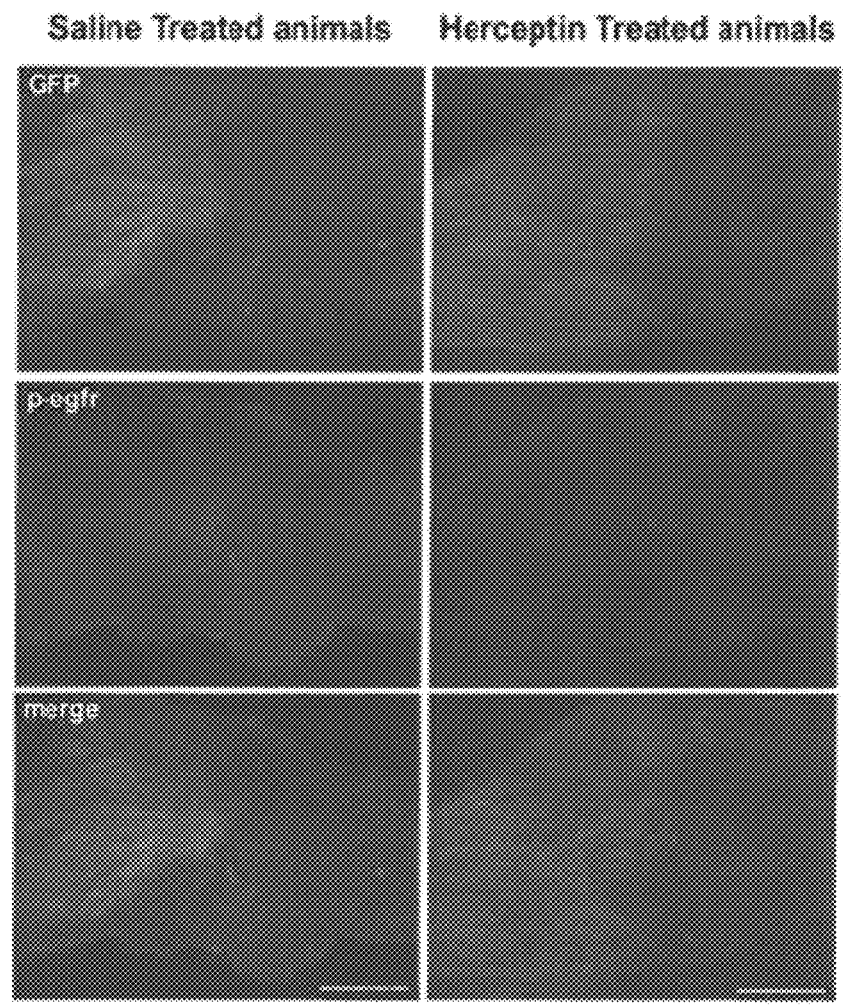
FIG. 10A shows immunofluorescent analysis revealed that the phosphorylated, activated form of EGFR was decreased in the proximal common peroneal nerve stump in rats treated systemically with Herceptin compared with saline controls.
Figure 10B:
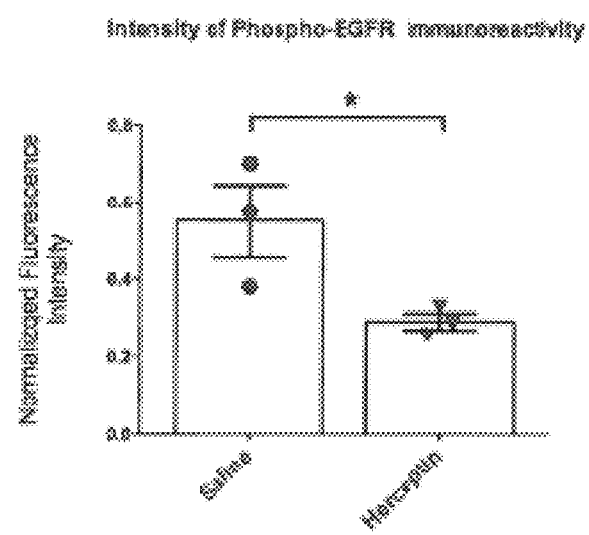
FIG. 10B shows objective analysis of the fluorescence intensity proximal to the repair sites, normalized against the GFP signal from the same section, revealed that there was a significant reduction in EGFR phosphorylation.

Immunofluorescent analysis revealed that the phosphorylated, activated form of EGFR was decreased in the proximal common peroneal nerve stump in rats treated systemically with Herceptin compared with saline controls (FIG. 10A). Objective analysis of the fluorescence intensity proximal to the repair sites, normalized against the GFP signal from the same section, revealed that there was a significant reduction in EGFR phosphorylation (FIG. 10B).

Discussion

Herceptin Administration Accelerates Motoneuron Regeneration and Myelinated Fiber Outgrowth into the Acutely Denervated Nerve Stump This disclosure used Herceptin, an inhibitor of ErbB2 in overexpressing breast cancers, to examine the role of neuregulin in peripheral nerve regeneration. Following acute transection with immediate repair, Herceptin increased the number of motoneurons that regenerated their axons at one week with a corresponding increase in the number of regenerated myelinated axons by four weeks (FIG. 3, FIG. 4, FIG. 5). Interestingly, this observed increase in regeneration peaked with a maximum number of motoneurons reached by two weeks post-repair. Herceptin either promoted the number of outgrowing axons or the rate of axonal outgrowth or both. The former is more likely as more axons were emitted per neuron. The structural characteristics of the regenerated axons were otherwise normal with respect to myelination and fiber diameter (FIG. 5B-FIG. 5E). Of note, our measurements of fiber diameter were smaller than previously reported values one month following crush injury (2.5 µm; Espejo & Alvarez, 1986) or transection injury (3.1 µm; Mackinnon, Dellon, & O'Brien, 1991) for both Herceptin and saline treated animals (2.06±0.05 µm and 2.00±0.04 µm; not significant). This likely resulted from the inclusion of a large number of small diameter fibers (on the order of ~1 µm) made possible by the high-resolution semi-automated counting method that permitted several thousand fibers to be sampled. However, the distribution of nerve fiber diameters was consistent with the unimodal distribution that typically occurs following regeneration (FIG. 5F)[37,39].

The overall extent of regeneration observed in these experiments was excellent when compared to the pool of uninjured motoneurons. After four weeks of regeneration, motoneuron counts reached 84% of uninjured controls (FIG. 3, dotted line). This is attributed to meticulous 2-suture epineurial repair, incorporating the repair site within a silicone cuff (see FIG. 1 for diagram) and rigid application of the criteria for counting motoneurons in the spinal cord. The technique of performing the repair within a cuff is believed to limit the extent of extraneural, misguided regeneration into the extraneural space and was demonstrated to be superior to repair without a cuff in a rat model[40].

Moreover, Herceptin increased the number of Bromodeoxyuridine (BrdU) labeled cells distal to the repair site with evidence of increased Schwann cell proliferation in response to Herceptin (FIG. 7). BrdU is only incorporated into the DNA of replicating cells, many of which were found to be Schwann cells based on nuclear morphology (FIG. 7E & FIG. 7F)[10,41,42]. This observation needs to be reconciled with the implications that GGF may not be necessary for sustained Schwann cell proliferation following injury and the fact that ErbB2 may be dispensable for Schwann cell proliferation altogether[10,28]. One explanation, as discussed below, is that Herceptin inhibits ErbB2 on a non-glial cell type that regulates Schwann cell proliferation. An alternative explanation is that ErbB2 signaling has a direct but mild inhibitory effect on Schwann cell proliferation that is prevented with Herceptin administration. However, this explanation is less likely given that specifically knocking out ErbB2 from the Schwann cell membrane has no impact on post-injury Schwann cell proliferation[28].

Taken together, these effects of Herceptin were surprising given its use as an ErbB2 inhibitor for the treatment of overexpressing breast cancers. Western blot analysis of whole nerve lysate revealed that Herceptin did not reduce the levels of total ErbB2 expression nor those of the phosphorylated, activated isoform of the protein (FIG. 6A), as shown previously in vitro[43,44]. These observations suggests that neuregulin signaling is not inhibited by Herceptin administration, a conclusion that is further supported the lack change in regenerated fiber myelination (g-ratio of 0.52±0.02 compared to >0.85 in neuregulin knockout models)[45].

In view of the negative findings on the Western blots, it was necessary to confirm the pharmacological activity of Herceptin. Herceptin is known to directly recruit the phosphatase PTEN to the intracellular plasma membrane, where it directly blocks the phosphorylation of the serine-threonine kinase Akt by phosphatidylinositol 3-kinase (PI3-K)[44,46]. This was tested in our whole nerve lysate and Herceptin was found to markedly reduce the amount of phosphorylated Akt, confirming its in vivo pharmacological activity (FIG. 6B).

Explanatory Hypothesis for the Pro-Regenerative and Mitogenic Effects of Herceptin Following Immediate Repair of a Transected Nerve.

The novel application of Herceptin, an inhibitory monoclonal antibody to the neuregulin receptor ErbB2, was expected to replicate the neuregulin knockout phenotype reported by Fricker et al.[45]. Paradoxically, it led to accelerated axonal outgrowth and Schwann cell proliferation. The explanation for these effects likely involves Herceptin's alteration of the relationships between ErbB already known to influence nerve regeneration. Given what is known, it is plausible that ErbB2 trans-activation of EGFR leads to inhibition of axon regeneration following nerve injury. Disinhibition by Herceptin to prevent this inhibitory heterodimerization may explain the effects observed. This hypothesis is based three lines of evidence.

Structural and Biochemical Data

ErbB2-EGFR readily forms heterodimers whose strong molecular interactions are stabilized in a region that is allosterically blocked by Herceptin following administration[15,16,23,50-52]. Trans-activation of EGFR by ErbB2 elicits a strong and unique signal compared to homodimers because ErbB2 decreases ligand dissociation[18,22,25]. Further, this strong trans-activation can be blocked by antibodies directed at the ErbB2 receptor[24].

Inhibitory Role of EGFR

There is a growing consensus that EGFR inhibits axon regeneration through a mechanism that involves trans-activation by an unknown factor[26,27,53-55]. In support of this, EGFR and ErbB2 are both expressed on the surface of peripheral motor and sensory neurons, as well as Schwann cells[56,57].

In Vivo and Molecular Data Presented in this Disclosure

Several observations in this disclosure support this hypothesis. The rate of motoneuron outgrowth with the administration of Herceptin was enhanced, but not the overall extent of regeneration. This would be consistent with a mechanism that enhances axonal elongation in the early phases, but where the normal regenerative processes eventually 'catch up'. This is similar to the effects published by Koprivica et al.[26], where EGFR inhibitors accelerated neurite outgrowth on inhibitory MAG, CSPG and OMgp substrates.

There were more myelinated fibers per motoneuron distal to the repair site in Herceptin treated animals than saline treated animals, suggesting more vigorous axonal outgrowth occurs in the presence of Herceptin. This is consistent the increased axonal outgrowth observed in vivo when EGFR inhibitors enhanced retinal ganglion cell axonal outgrowth[26] and nrg-1 knockout mice that demonstrated increased collateral sprouting at the neuromuscular junction[45].

Schwann cell proliferation may also be accounted for by earlier and more vigorous axonal extension into the distal nerve, leading to an effect similar to the second wave of Schwann cell proliferation observed by Pellegrino and Spencer[8]. It is also possible that Herceptin may have an independent mitogenic influence on Schwann cells, separate from the proposed effects on axonal elongation.

This hypothesis is also supported by the inventors in vitro data that suggests these pro-regenerative effects of Herceptin are independent of neuregulin signaling. Interestingly, recent in vitro data has also shown that siRNA knockdown of EGFR in cultured neonatal rat neurons significantly reduced Akt phosphorylation[58], similar to what was observed in our disclosure.

Taken together, this accumulation of evidence may suggest an expanded role for the ErbB2 receptor in peripheral nerve regeneration in addition to transducing signals for axon-driven re-myelination. This new role of the ErbB2 receptor may function to dampen overly vigorous regeneration that would lead to extensive and inefficient sprouting in the early phases of regeneration. It is interesting to speculate about this possible dual function of the ErbB2 receptor later in regeneration where it could serve as a maturation signal that prompts axons to stop elongating and Schwann cell to start myelinating.

Alternative Explanations

The inventors have also considered alternative explanations for the observed pro-regenerative effects of Herceptin. First, it is possible that the effects of Herceptin primarily influenced Schwann cell and macrophage proliferation which may have accelerated debris clearance during Wallerian degeneration[59,60]. Faster 'priming' of endoneurial channels for regeneration may have increased the rate of initial axonal outgrowth, but this cannot account for the in vitro observations made. Alternatively, Herceptin may prevent the formation of ErbB2-ErbB4 heterodimers which have been shown to inhibit axonal elongation in development[61]. However, ErbB4 mRNA expression and protein detection is effectively absent in the regenerating peripheral nerve following injury in mature animals[10,56]. A last alternative would be that Herceptin operates through some undescribed pathway unrelated to ErbB receptor signaling.

The Lack of Influence on Chronically Axotomized Proximal Nerve Stumps is Evidence of Herceptin's Site of Action and a Possible Decline in Neuronal ErbB2 Expression.

Herceptin administration accelerated axonal outgrowth in acutely axotomized motoneurons but not chronically axotomized motoneurons when compared after two weeks of regeneration. Importantly, this observation indicates that Herceptin acts on either neurons or Schwann cells in the proximal stump, as the denervated distal stumps were no different between the two groups. Herceptin's action on neuronal ErbB2 would support the hypothesis that Herceptin prevents the inhibitory trans-activation of EGFR by ErbB2. However, a Schwann cell targeted effect cannot be ruled out. For example, Herceptin could increase the mobilization of Schwann cells to the 'outgrowth zone' of the proximal stump and accelerate the co-migration with axons across the repair site[62,63]. The fact that Herceptin lost its pro-regenerative influence after four months of chronic axotomy would be most consistent with a decline in ErbB2 over this period. While Schwann cell ErbB2 expression is known to decrease over several months following injury[12,56,64], little is known about neuronal ErbB2 expression patterns during chronic axotomy.

Controversy exists regarding the specific regulatory function of neuregulin and its receptor ErbB2 in peripheral nerve regeneration. The present inventors tested the hypothesis that inhibition of the ErbB2 receptor with the novel application of Herceptin would diminish neuregulin signaling and regenerative outcomes in the setting of acute and chronic denervation. It was believed that the experimental model used by the inventors offered an efficient alternative to transgenic knockout models that are associated with a lethal double-mutant phenotype. Paradoxically, Herceptin accelerated the rate of axon regeneration, increased the overall extent of distal axonal outgrowth and was found to increase Schwann cell proliferation in the distal nerve stump. This data suggests that the site of action may also localize to neurons in the proximal stump of the injured nerve. Of interest, the proposed explanation for these effects involved an novel inhibitory role for ErbB2 whereby it associates with EGFR within an inhibitory heterodimer whose formation is blocked with Herceptin administration. In support of this, our immunohistochemical analysis indeed shows a significant reduction in the levels of activated, phosphorylated EGFR in nerve sections from rats treated with Herceptin. Specifically, this reduction occurs in the axotomized stump proximal to the repair site. This is also consistent with our previous conclusion that Herceptin exerts its influence on neurons in the proximal stump and is supported by the described structural and biochemical evidence from the literature.

According to the experiment of the present inventors, a potential new role for the ErbB2 receptor was investigated where its function is centralized between the positive regulation of axonal outgrowth and myelination through neuregulin signaling and possible mediating the inhibitory axon on axonal outgrowth of EGFR. The findings in this disclosure provide evidence for the first description of ErbB2 negatively regulating axonal outgrowth through its potential inhibitory association with the EGFR receptor. Provided this model is valid, EGFR-ErbB2 dis-inhibition with a monoclonal antibody has also never been demonstrated in vivo within the peripheral nervous system. Last, the findings in this disclosure suggest that ErbB2 participates in Schwann cell proliferation indirectly by increasing axonal contact due to the accelerated outgrowth seen with Herceptin administration.

In this disclosure, the dosing regimen for administrating Herceptin into rats was intraperitoneal injections of 8 mg/kg every 3 days. In human subjects, the inhibitor of ErbB2 according to the present disclosure can be systemically administered. It is well known that systemic administration mean providing a medication that circulates throughout the body to which most of the tissues of the body are exposed. Herceptin, which is used in the embodiment of the present disclosure, is FDA approved for intravenous administration to human subjects. Therefore, intravenous administration of the inhibitor of ErbB2 according to the present disclosure can be used for human application to treat nerve injuries.

In human application, the inhibitor of ErbB2 according the present disclosure may be administered in a dosage of about 4 mg/kg loading dose followed by weekly maintenance doses of 2 mg/kg. Alternatively, an 8 mg/kg loading dose followed by 6 mg/kg maintenance dosing every three weeks may be considered. This may be provided by dilution in 250 mL of 0.9% NaCl (saline) and administering over a 90-minute infusion period. This regimen is similar to that used in the chemotherapeutic administration of Herceptin for breast cancer.

In one embodiment of the present disclosure, the inhibitor of ErbB2 according the present disclosure may be administered after the injury before or after surgical intervention. In another embodiment of the present disclosure, the inhibitor of ErbB2 according the present disclosure may be administered in the absence of a surgical intervention.

LITERATURE CITED

1. Jessen K R, Mirsky R. Schwann cells and their precursors emerge as major regulators of nerve development. *Trends Neurosci.* 1999; 22(9):402-410.
2. Jessen K R, Mirsky R. The origin and development of glial cells in peripheral nerves. *Nat Rev Neurosci.* 2005; 6(9):671-682. doi:10.1038/nrn1746.
3. Jessen K R, Mirsky R. Negative regulation of myelination: relevance for development, injury, and demyelinating disease. *Glia.* 2008; 56(14):1552-1565. doi:10.1002/glia.20761.
4. Stoll G, Müller H W. Nerve injury, axonal degeneration and neural regeneration: basic insights. *Brain Pathol.* 1999; 9(2):313-325.
5. Arthur-Farraj P J, Latouche M, Wilton D K, et al. c-Jun reprograms Schwann cells of injured nerves to generate a repair cell essential for regeneration. *Neuron.* 2012; 75(4): 633-647. doi:10.1016/j.neuron.2012.06.021.

6. Mirsky R, Jessen K R, Brennan A, et al. Schwann cells as regulators of nerve development. *J Physiol Paris.* 2002; 96(1-2):17-24.
7. Arthur-Farraj P, Wanek K, Hantke J, et al. Mouse schwann cells need both NRG1 and cyclic AMP to myelinate. *Glia.* 2011; 59(5):720-733. doi:10.1002/glia.21144.
8. Pellegrino R G, Spencer P S. Schwann cell mitosis in response to regenerating peripheral axons in vivo. *Brain Res.* 1985; 341(1):16-25.
9. Michailov G V, Sereda M W, Brinkmann B G, et al. Axonal neuregulin-1 regulates myelin sheath thickness. *Science (80-).* 2004; 304(5671):700-703.
10. Carroll S L, Miller M L, Frohnert P W, Kim S S, Corbett J a. Expression of neuregulins and their putative receptors, ErbB2 and ErbB3, is induced during Wallerian degeneration. *J Neurosci.* 1997; 17(5):1642-1659.
11. Morrissey T K, Levi A D, Nuijens A, Sliwkowski M X, Bunge R P. Axon-induced mitogenesis of human Schwann cells involves heregulin and p185erbB2. *Proc Natl Acad Sci USA.* 1995; 92(5):1431-1435.
12. Li H, Wigley C, Hall S M. Chronically denervated rat Schwann cells respond to GGF in vitro. *Glia.* 1998; 24(3):290-303.
13. Falls D L. Neuregulins: functions, forms, and signaling strategies. *Exp Cell Res.* 2003; 284(1):14-30. doi:10.1016/S0014-4827(02)00102-7.
14. Yarden Y, Sliwkowski M X. Untangling the ErbB signalling network. *Nat Rev Mol Cell Biol.* 2001; 2(2):127-137. doi:10.1038/35052073.
15. Garrett T P J, Mckern N M, Lou M, et al. The Crystal Structure of a Truncated ErbB2 Ectodomain Reveals an Active Conformation, Poised to Interact with Other ErbB Receptors. *Mol Cell.* 2003; 11:495-505.
16. Garrett T P J, McKern N M, Lou M, et al. Crystal structure of a truncated epidermal growth factor receptor extracellular domain bound to transforming growth factor alpha. *Cell.* 2002; 110(6):763-773.
17. Olayioye M A, Neve R M, Lane H A, Hynes N E. The ErbB signaling network: receptor heterodimerization in development and cancer. *EMBO J.* 2000; 19(13):3159-3167.
18. Karunagaran D, Tzahar E, Beerli R R, et al. ErbB-2 is a common auxiliary subunit of NDF and EGF receptors: implications for breast cancer. *EMBO J.* 1996; 15(2):254-264.
19. Linggi B, Carpenter G. ErbB receptors: new insights on mechanisms and biology. *Trends Cell Biol.* 2006; 16(12):649-656. doi:10.1016/j.tcb.2006.10.008.
20. Roskoski R. The ErbB/HER family of protein-tyrosine kinases and cancer. *Pharmacol Res.* 2014; 79(epub ahead of print):34-74. doi:10.1016/j.phrs.2013.11.002.
21. Macdonald-Obermann J L, Piwnica-Worms D, Pike L J. Mechanics of EGF receptor/ErbB2 kinase activation revealed by luciferase fragment complementation imaging. *Proc Natl Acad Sci USA.* 2012; 109(1):137-142. doi:10.1073/pnas.1111316109.
22. Olayioye M a, Graus-Porta D, Beerli R R, Rohrer J, Gay B, Hynes N E. ErbB-1 and ErbB-2 acquire distinct signaling properties dependent upon their dimerization partner. *Mol Cell Biol.* 1998; 18(9):5042-5051.
23. Citri A, Skaria K B, Yarden Y. The deaf and the dumb: the biology of ErbB-2 and ErbB-3. *Exp Cell Res.* 2003; 284(1):54-65. doi:10.1016/S0014-4827(02)00101-5.
24. Klapper L N, Vaisman N, Hurwitz E, Pinkas-kramarski R, Yarden Y, Sela M. A subclass of tumor-inhibitory monoclonal antibodies to ErbB-2/HER2 blocks crosstalk with growth factor receptors. *Oncogene.* 1997; 14:2099-2109.
25. Pinkas-Kramarski R, Soussan L, Waterman H, et al. Diversification of Neu differentiation factor and epidermal growth factor signaling by combinatorial receptor interactions. *EMBO J.* 1996; 15(10):2452-67.
26. Koprivica V, Cho K-S, Park J B, et al. EGFR activation mediates inhibition of axon regeneration by myelin and chondroitin sulfate proteoglycans. *Science.* 2005; 310 (5745):106-110. doi:10.1126/science.1115462.
27. Leinster V H L, Joy M T, Vuononvirta R E, Bolsover S R, Anderson P N. ErbB1 epidermal growth factor receptor is a valid target for reducing the effects of multiple inhibitors of axonal regeneration. *Exp Neurol.* 2013; 239:82-90. doi:10.1016/j.expneurol.2012.09.007.
28. Atanasoski S, Scherer S S, Sirkowski E, et al. ErbB2 signaling in Schwann cells is mostly dispensable for maintenance of myelinated peripheral nerves and proliferation of adult Schwann cells after injury. *J Neurosci.* 2006; 26(7):2124-2131. doi:10.1523/JNEUROSCI4594-05.2006.
29. Fendly B M, Winget M, Hudziak R M, Lipari M T, Napier M A, Ullrich A. Characterization of Murine Monoclonal Antibodies Reactive to Either the Human Epidermal Growth Factor Receptor or HER2/neu Gene Product. *Cancer Res.* 1990; 50:1550-1558.
30. Carter P, Presta L, Gorman C M, et al. Humanization of an anti-p185HER2 antibody for human cancer therapy. *Proc Natl Acad Sci USA.* 1992; 89(10):4285-4289.
31. Baselga J, Tripathy D, Mendelsohn J, et al. Phase II study of weekly intravenous recombinant humanized anti-p185HER2 monoclonal antibody in patients with HER2/neu-overexpressing metastatic breast cancer. *J Clin Oncol.* 1996; 14(3):737-744.
32. Pegram M, Ngo D. Application and potential limitations of animal models utilized in the development of trastuzumab (Herceptin): a case study. *Adv Drug Deliv Rev.* 2006; 58(5-6):723-734. doi:10.1016/j.addr.2006.05.003.
33. Güler M, Yilmaz T, Ozercan I, Elkiran T. The inhibitory effects of trastuzumab on corneal neovascularization. *Am J Ophthalmol.* 2009; 147(4):703-708.e2. doi:10.1016/j.ajo.2008.09.022.
34. Frank R T, Edmiston M, Kendall S E, et al. Neural stem cells as a novel platform for tumor-specific delivery of therapeutic antibodies. *PLoS One.* 2009; 4(12):e8314. doi:10.1371/journal.pone.0008314.
35. Sulaiman O a. R, Midha R, Munro C a., Matsuyama T, Al-Majed A, Gordon T. Chronic Schwann Cell Denervation and the Presence of a Sensory Nerve Reduce Motor Axonal Regeneration. *Exp Neurol.* 2002; 176(2):342-354. doi:10.1006/exnr.2002.7928.
36. Furey M J, Midha R, Xu Q-G, Belkas J, Gordon T. Prolonged target deprivation reduces the capacity of injured motoneurons to regenerate. *Neurosurgery.* 2007; 60(4):723-32; discussion 732-3. doi:10.1227/01.NEU.0000255412.63184.CC.
37. Espejo F, Alvarez J. Microtubules and calibers in normal and regenerating axons of the sural nerve of the rat. *J Comp Neurol.* 1986; 250(1):65-72. doi:10.1002/cne.902500106.
38. Mackinnon S E, Dellon A L, O'Brien J P. Changes in nerve fiber numbers distal to a nerve repair in the rat sciatic nerve model. *Muscle Nerve.* 1991; 14(11):1116-22. doi:10.1002/mus.880141113.

39. Aitken J T, Sharman M, Young J Z. Maturation of Regenerating Nerve Fibres with Various Peripheral Connexions. *Journa Anat.* 1947; 81(1):1-22.
40. Sulaiman O A R, Gordon T. Transforming growth factor-beta and forskolin attenuate the adverse effects of long-term Schwann cell denervation on peripheral nerve regeneration in vivo. *Glia.* 2002; 37(3):206-218. doi: 10.1002/glia.10022.
41. Bradley W G, Asbury A K. Duration of synthesis phase in neurilemma cells in mouse sciatic nerve during degeneration. *Exp Neurol.* 1970; 26(2):275-282.
42. Asbury A K. Schwann cell proliferation in developing mouse sciatic nerve: a radioautographic study. *J Cell Biol.* 1967; 34(3):735-743.
43. Agus D B, Akita R W, Fox W D, et al. Targeting ligand-activated ErbB2 signaling inhibits breast and prostate tumor growth. *Cancer Cell.* 2002; 2(2):127-137.
44. Longva K E, Pedersen N M, Haslekås C, Stang E, Madshus I H. Herceptin-induced inhibition of ErbB2 signaling involves reduced phosphorylation of Akt but not endocytic down-regulation of ErbB2. *Int J cancer.* 2005; 116(3):359-367. doi:10.1002/ijc.21015.
45. Fricker F R, Lago N, Balarajah S, et al. Axonally derived neuregulin-1 is required for remyelination and regeneration after nerve injury in adulthood. *J Neurosci.* 2011; 31(9):3225-3233. doi:10.1523/JNEUROSCI2568-10.2011.
46. Nagata Y, Lan K-H, Zhou X, et al. PTEN activation contributes to tumor inhibition by trastuzumab, and loss of PTEN predicts trastuzumab resistance in patients. *Cancer Cell.* 2004; 6(2):117-27. doi:10.1016/j.ccr.2004.06.022.
49. Atanasoski S, Shumas S, Dickson C, Scherer S S, Suter U. Differential cyclin D1 requirements of proliferating Schwann cells during development and after injury. *Mol Cell Neurosci.* 2001; 18(6):581-592. doi:10.1006/mcne.2001.1055.
50. Ogiso H, Ishitani R, Nureki O, et al. Crystal structure of the complex of human epidermal growth factor and receptor extracellular domains. *Cell.* 2002; 110(6):775-787.
51. Cho H, Mason K, Ramyar K X, et al. Structure of the extracellular region of HER2 alone and in complex with the Herceptin Fab. *Nature.* 2003; 421(February):756-760. doi:10.1038/nature01423.Published.
52. Cho H, Leahy D J. Structure of the extracellular region of HER3 reveals an interdomain tether. *Science* (80-). 2002; 297(5585):1330-1333.
53. Berry M, Ahmed Z, Douglas M R, Logan A. Epidermal growth factor receptor antagonists and CNS axon regeneration: mechanisms and controversies. *Brain Res Bull.* 2011; 84(4-5):289-299. doi:0.1016/j.brainresbull.2010.08.004.
54. Douglas M R, Morrison K C, Jacques S J, et al. Off-target effects of epidermal growth factor receptor antagonists mediate retinal ganglion cell disinhibited axon growth. *Brain.* 2009; 132(Pt 11):3102-3121. doi: 10.1093/brain/awp240.
55. Ahmed Z, Jacques S J, Berry M, Logan A. Epidermal growth factor receptor inhibitors promote CNS axon growth through off-target effects on glia. *Neurobiol Dis.* 2009; 36(1):142-150. doi:10.1016/j.nbd.2009.07.016.
56. Audisio C, Nicolino S, Scevola A, et al. ErbB receptors modulation in different types of peripheral nerve regeneration. *Neuroreport.* 2008; 19(16):1605-1609. doi: 10.1097/WNR.0b013e32831313ef.
57. Pearson R J, Carroll S L. ErbB transmembrane tyrosine kinase receptors are expressed by sensory and motor neurons projecting into sciatic nerve. *J Histochem Cytochem.* 2004; 52(10):1299-1311. doi:10.1369/jhc.3A6208.2004.
58. Xu M-F, Zhou H, Hu C-Y, Liang Y-Q, Hu L, Chen D. The mechanisms of EGFR in the regulation of axon regeneration. *Cell Biochem Funct.* 2014; 32(1):101-105. doi:10.1002/cbf.2977.
59. Gaudet A D, Popovich P G, Ramer M S. Wallerian degeneration: gaining perspective on inflammatory events after peripheral nerve injury. *J Neuroinflammation.* 2011; 8(1):110-123. doi:10.1186/1742-2094-8-110.
60. Stoll G, Griffin J W, Li C Y, Trapp B D. Wallerian degeneration in the peripheral nervous system: participation of both Schwann cells and macrophages in myelin degradation. *J Neurocytol.* 1989; 18(5):671-683.
61. Pinkas-Kramarski R, Eilam R, Alroy I, Levkowitz G, Lonai P, Yarden Y. Differential expression of NDF/neuregulin receptors ErbB-3 and ErbB-4 and involvement in inhibition of neuronal differentiation. *Oncogene.* 1997; 15(23):2803-2815. doi:10.1038/sj.onc.1201466.
62. Cheng C, Zochodne D W. In vivo proliferation, migration and phenotypic changes of Schwann cells in the presence of myelinated fibers. *Neuroscience.* 2002; 115(1):321-329.
63. Chen Y Y, McDonald D, Cheng C, Magnowski B, Durand J, Zochodne D W. Axon and Schwann cell partnership during nerve regrowth. *J Neuropathol Exp Neurol.* 2005; 64(7):613-622.
64. Li H, Terenghi G, Hall S M. Effects of delayed re-innervation on the expression of c-erbB receptors by chronically denervated rat Schwann cells in vivo. *Glia.* 1997; 20(4):333-347.

The invention claimed is:
1. A method of enhancing survival of a nerve and/or nerve tissue, the method comprising:
   a) administering an inhibitor of the ErbB2 receptor to a mammal who has sustained nerve injury; and
   b) examining the mammal for motor or sensory neuron survival in response to administration of the inhibitor, wherein said inhibitor of the ErbB2 receptor is Trastuzumab.
2. The method of claim 1, wherein administration of the inhibitor comprises systemically administering the inhibitor to the mammal.
3. The method of claim 1, wherein the step (a) comprises administering the inhibitor to the mammal before or after a surgical intervention.
4. The method of claim 1, wherein the nerve and/or nerve tissue injury is a result of physical trauma or the result of a physical injury.
5. The method of claim 1, further comprising a step of examining if the antibody further inhibits trans-activation of the EGFR receptor by ErbB2, wherein the mammal is non-human.
6. A method of accelerating axonal outgrowth and/or increasing motor or sensory neuron or glial survival after nerve injury, the method comprising:
   a) exposing a nerve of a mammal to an inhibitor of the ErbB2 receptor; and
   b) examining the mammal for accelerated axonal outgrowth and/or increased neuron or glial survival after the exposing of the nerve to the inhibitor, wherein said inhibitor of the ErbB2 receptor is Trastuzumab.

7. The method of claim 6, wherein exposing the nerve to the inhibitor comprises systemically administering the inhibitor to the mammal.

8. A method of increasing Schwann cell proliferation in a nerve stump, the method comprising:
   a) administering to a mammal an inhibitor of the ErbB2 receptor; and
   b) examining the mammal for increased Schwann cell proliferation in a nerve stump in response to administration of the inhibitor,
   wherein said inhibitor of the ErbB2 receptor is Trastuzumab.

9. The method of claim 8, wherein said administration is systemic administration to the mammal.

* * * * *